United States Patent
Kasahara et al.

(10) Patent No.: US 11,903,772 B2
(45) Date of Patent: Feb. 20, 2024

(54) ULTRASONIC DIAGNOSTIC SYSTEM

(71) Applicant: FUJIFILM Healthcare Corporation, Kashiwa (JP)

(72) Inventors: Eiji Kasahara, Chiba (JP); Koji Waki, Chiba (JP); Akira Kusakabe, Chiba (JP); Suguru Ishiguro, Chiba (JP)

(73) Assignee: FUJIFILM Healthcare Corporation, Chiba (JP)

( * ) Notice: Subject to any disclaimer, the term of this patent is extended or adjusted under 35 U.S.C. 154(b) by 0 days.

(21) Appl. No.: 17/589,946

(22) Filed: Feb. 1, 2022

(65) Prior Publication Data

US 2022/0249067 A1 Aug. 11, 2022

(30) Foreign Application Priority Data

Feb. 9, 2021 (JP) ................................. 2021-018827

(51) Int. Cl.
*A61B 8/00* (2006.01)
*G16H 80/00* (2018.01)

(52) U.S. Cl.
CPC .............. *A61B 8/565* (2013.01); *A61B 8/461* (2013.01); *A61B 8/468* (2013.01); *G16H 80/00* (2018.01)

(58) Field of Classification Search
CPC ......... A61B 8/565; A61B 8/461; A61B 8/468; G16H 80/00
See application file for complete search history.

(56) References Cited

U.S. PATENT DOCUMENTS

| 6,514,201 B1* | 2/2003 | Greenberg | G01S 7/52023 |
| | | | 600/437 |
| 2008/0249401 A1 | 10/2008 | Watanabe et al. | |
| 2014/0275954 A1* | 9/2014 | Ohta | A61B 5/0071 |
| | | | 600/407 |
| 2014/0282018 A1* | 9/2014 | Amble | G16H 40/63 |
| | | | 715/733 |
| 2015/0035959 A1* | 2/2015 | Amble | A61B 5/0077 |
| | | | 348/74 |
| 2016/0143626 A1 | 5/2016 | Ohta et al. | |
| 2019/0059851 A1* | 2/2019 | Rothberg | A61B 8/42 |
| 2020/0069291 A1* | 3/2020 | Zaslavsky | A61B 8/4245 |

(Continued)

FOREIGN PATENT DOCUMENTS

| JP | 2001-276061 A | 10/2001 |
| JP | 2003-265454 A | 9/2003 |

(Continued)

OTHER PUBLICATIONS

Japanese official action dated Oct. 24, 2023 (and machine translation thereof into English language) in connection with corresponding Japanese Patent Application No. 2021-018827.

*Primary Examiner* — Jennifer N Welch
*Assistant Examiner* — Reji Kartholy
(74) *Attorney, Agent, or Firm* — Paul Teng

(57) ABSTRACT

An ultrasonic diagnostic device is provided in an examination room, and a remote device is provided in another room. The remote device has a conversion unit that converts advice (voice) from an advisor into a character string. Data indicating the character string are transmitted from the remote device to the ultrasonic diagnostic device. The character string is displayed on a display device of the ultrasonic diagnostic device. An advisor image is also displayed on the display device.

5 Claims, 6 Drawing Sheets

(56) References Cited

U.S. PATENT DOCUMENTS

| | | | |
|---|---|---|---|
| 2020/0187913 A1* | 6/2020 | Liu | G16H 80/00 |
| 2020/0229798 A1 | 7/2020 | Leyvi et al. | |
| 2021/0020181 A1* | 1/2021 | Gorny | G10L 17/00 |
| 2023/0316751 A1* | 10/2023 | Schmidt | A61B 5/742 |
| | | | 382/103 |

FOREIGN PATENT DOCUMENTS

| | | |
|---|---|---|
| JP | 4698423 B | 3/2011 |
| JP | 2015-29620 A | 2/2015 |
| JP | 2016-042289 A | 3/2016 |
| JP | 2017-209339 A | 11/2017 |
| JP | 2019-145936 A | 8/2019 |
| JP | 2020-508195 A | 3/2020 |

* cited by examiner

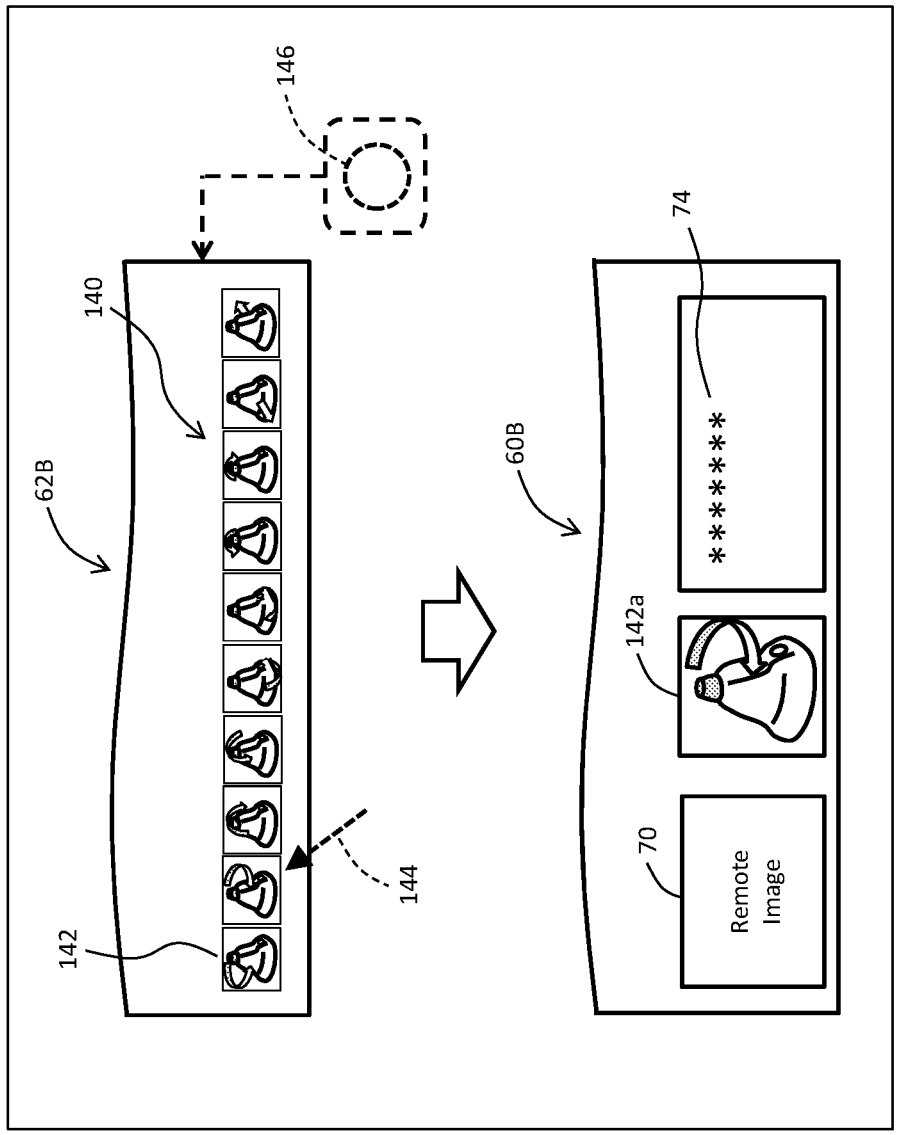

ULTRASONIC DIAGNOSTIC SYSTEM

CROSS REFERENCE TO RELATED APPLICATION

This application claims priority to Japanese Patent Application No. 2021-018827 filed on Feb. 9, 2021, which is incorporated herein by reference in its entirety including the specification, claims, drawings, and abstract.

TECHNICAL FIELD

The present disclosure relates to an ultrasonic diagnostic system, and in particular to an ultrasonic diagnostic system including an ultrasonic diagnostic device and a remote device.

BACKGROUND

An ultrasonic diagnostic device is a medical device that generates an ultrasonic image based on a received signal obtained by transmitting ultrasonic waves to the subject and receiving waves reflected from the inside of the body of the subject. The ultrasonic diagnostic device has a probe. Typically, a transmitting and receiving surface of the probe is applied to a surface of the subject, and in this state, the probe transmits and receives ultrasonic waves. Although to obtain an appropriate ultrasonic image, it is necessary to precisely adjust a position or posture of the probe with respect to a target tissue, doing so quickly and accurately requires skill. When an inexperienced examiner performs ultrasonic examination, advice from a well experienced expert is necessary.

Patent Document 1 (JP 2015-29620 A) and Patent Document 2 (JP 4698423 B) disclose a remote medical system. These documents nowhere disclose a feature of transmitting advice for ultrasonic diagnosis.

CITATION LIST

Patent Literature

Patent Document 1: JP 2015-296520 A
Patent Document 2: JP 4698423 B

SUMMARY

In ultrasonic examination, when an advisor gives advice to the examiner, and the content of the advice is conveyed to the subject, the subject may feel anxiety. In addition, direct oral instructions to the examiner in the examination room may cause stress to the examiner.

An object of the present disclosure is to prevent easy conveyance, to the subject, of the content of advice given from the advisor to the examiner. Alternatively, an object of the present disclosure is to reduce stress of the examiner who receives advice.

An ultrasonic diagnostic system according to the present disclosure includes an ultrasonic diagnostic device operated by an examiner, and a remote device that is connected to the ultrasonic diagnostic device via a communication line and operated by an advisor who gives advice to the examiner. In this system, the ultrasonic diagnostic device has a probe that transmits and receives ultrasonic waves, a first display device that displays an ultrasonic image generated by transmitting and receiving the ultrasonic waves, and a first communication unit that transmits image data for displaying the ultrasonic image to the remote device. The remote device has a second communication unit that receives the image data, a second display device that displays the ultrasonic image based on the image data, and a microphone that converts the voice of the advisor to an audio signal. In this system, a conversion unit that converts the audio signal to an advice character string is provided, and the advice character string is displayed on the first display device while ultrasonic examination is being performed by the examiner.

BRIEF DESCRIPTION OF DRAWINGS

Embodiments of the present disclosure will be described based on the following FIGURES, wherein:

FIG. 7 is a diagram showing a display example according to the second embodiment.

DESCRIPTION OF EMBODIMENTS

Figure 1:
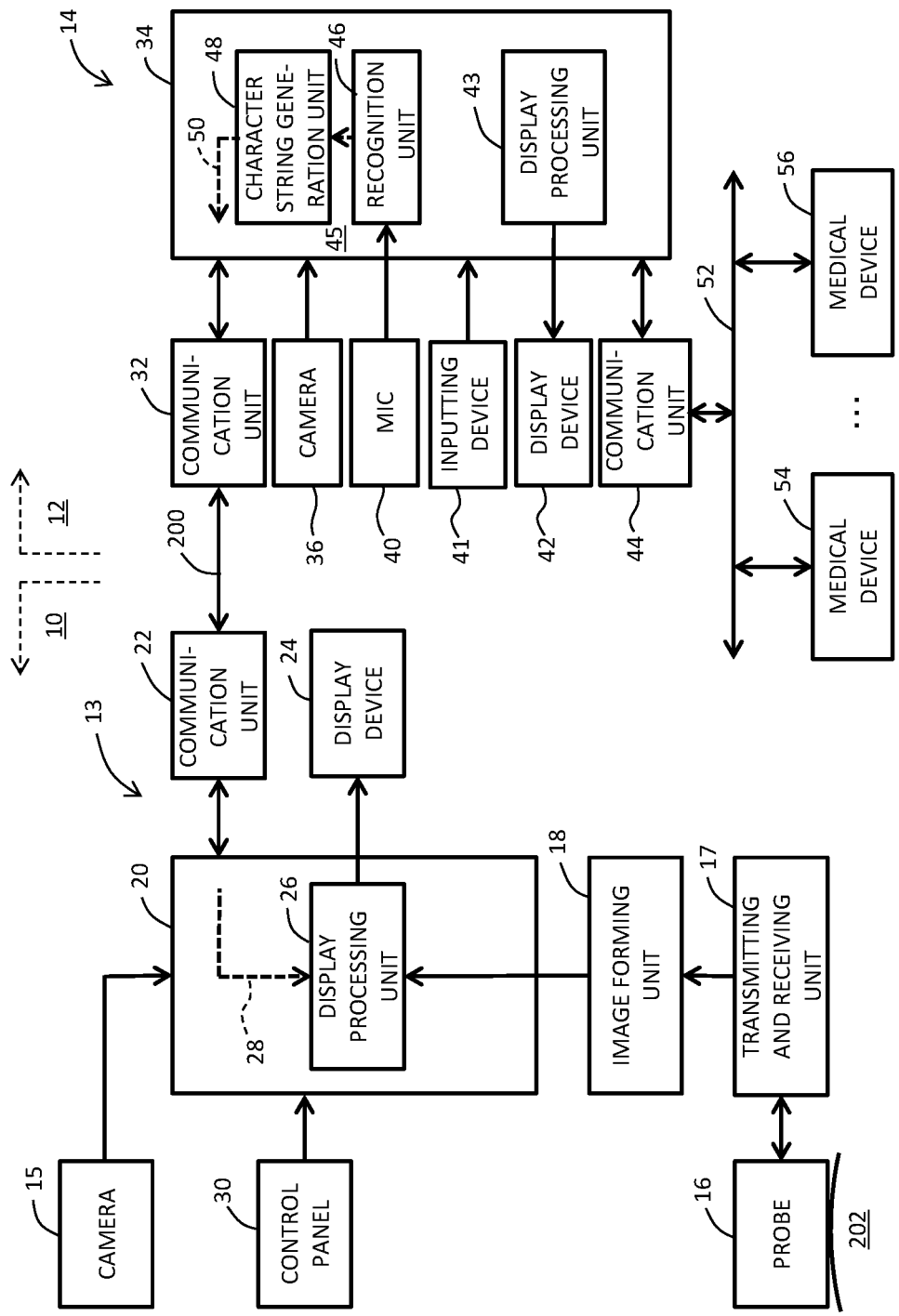
FIG. 1 is a block diagram showing a configuration of an ultrasonic diagnostic system according to a first embodiment.

Hereinafter, embodiments will be described with reference to the drawings.

(1) Summary of Embodiments

An ultrasonic diagnostic system according to an embodiment has an ultrasonic diagnostic device operated by an examiner, and a remote device that is connected to the ultrasonic diagnostic device via a communication line and operated by an advisor who gives advice to the examiner. The ultrasonic diagnostic device has a probe that transmits and receives ultrasonic waves, a first display device that displays an ultrasonic image generated by transmitting and receiving the ultrasonic waves, and a first communication unit that transmits image data for displaying the ultrasonic image to the remote device. The remote device has a second communication unit that receives the image data, a second display device that displays the ultrasonic image based on the image data, and a microphone that converts the voice of the advisor to an audio signal. The ultrasonic diagnostic system according to the embodiment further has a conversion unit that converts the audio signal to an advice character string. The advice character string is displayed on the first display device while ultrasonic examination is being performed by the examiner.

In this manner, the advice is communicated to the examiner in the form of character string instead of voice. The content of the advice is thus not easily conveyed to the subject, and therefore, the possibility that the subject feels anxiety due to the advice can be reduced. The advice in the form of character string may also cause less stress on the examiner, as compared to oral advice. Furthermore, as a space inside the examination room is generally not very large, the above feature achieves an advantage of avoiding human congestion in the examination room.

In the embodiment, the conversion unit is provided in the remote device. Data indicating the advice character string are transmitted from the second communication unit to the first communication unit. This feature allows a reduction in the amount of information to be transmitted.

In the embodiment, the remote device includes a remote camera that obtains an image of the advisor. Advisor image data output from the remote camera are transmitted from the second communication unit to the first communication unit. The advisor image is displayed on the first display device together with the advice character string. This feature enables the examiner to observe an attitude and expression of the advisor and achieve a sense of ease. The feature also enables provision of, for example, guidance on probe operation by using gestures.

The ultrasonic diagnostic system according to the embodiment has a local camera that captures an image of the subject to whom the probe is applied and obtains a subject image. Subject image data output from the local camera are transmitted from the first communication unit to the second communication unit. The subject image is displayed on the second display device together with the ultrasonic image. This enables the advisor to visually recognize a position and posture of the probe and a posture of the subject.

In the embodiment, the ultrasonic diagnostic device includes a plurality of response elements to be selected by the examiner. Response information corresponding to a response element selected from the plurality of response elements is transmitted from the first communication unit to the second communication unit. A response character string based on the response information is displayed on the second display device. The plurality of response elements are a plurality of actual or virtual controls selected by a trackball, a switching operation, or the like. This allows bi-directional communication between the examiner and the advisor. The response information is composed of data indicating the response character string, a code for specifying the response character string, and the like.

In the embodiment, an operation support image selected by the advisor is displayed on the first display device together with the advice character string. This facilitates, in particular, understanding of the content of advice concerning probe operation. A probe simulation image may be selected from a plurality of probe simulation images (including display elements indicating operation directions) by the advisor, and data or a code indicating the selected probe simulation image may be transmitted from the remote device to the ultrasonic diagnostic device. In an embodiment, an ultrasonic diagnostic device is operated by an examiner. The ultrasonic diagnostic device is connected to a remote device operated by the advisor who gives advice to the examiner via a communication line. The ultrasonic diagnostic device has a probe that transmits and receives ultrasonic waves, a display device that displays an ultrasonic image generated by transmitting and receiving the ultrasonic waves, and a communication unit that transmits image data for displaying the ultrasonic image to the remote device and receives character string data representing the voice of the advisor from the remote device. An advice character string based on the character string data is displayed on the display device while ultrasonic examination is being performed by the examiner.

In an embodiment, a remote device is operated by an advisor who gives advice to an examiner. The remote device is connected to an ultrasonic diagnostic device operated by an examiner via a communication line. The remote device has a microphone that converts the voice of the advisor to an audio signal, a conversion unit that converts the audio signal to character string data, a communication unit that receives image data from the ultrasonic diagnostic device and transmits the character string data to the ultrasonic diagnostic device, and a display device that displays an ultrasonic image based on the image data. An advice character string based on the character string data is displayed on a display device of the ultrasonic diagnostic device while ultrasonic examination is being performed by the examiner.

(2) Details of Embodiments

FIG. 1 shows an ultrasonic diagnostic system according to an embodiment. This ultrasonic diagnostic system is installed in a medical facility, such as a hospital. The medical facility includes an examination room 10 and another room 12. The examination room 10 and the room 12 may be adjacent to each other or may be separated from each other.

The ultrasonic diagnostic system is composed of an ultrasonic diagnostic device 13 and a remote device 14. The remote device 14 is an information processing device, such as, for example, a tablet terminal. The remote device 14 may be present in a room in a different building.

In the examination room 10, a bed is placed, and the ultrasonic diagnostic device 13 is placed in the vicinity of it. The subject lies on the bed. The ultrasonic diagnostic device 13 is operated by an examiner (doctor or medical technician). Meanwhile, the remote device 14 is operated by an advisor (doctor or medical technician). For example, the examiner is a person who has insufficient experience in ultrasonic examination, while the adviser is a person who has abundant experience in ultrasonic examination (expert). The examiner performs ultrasonic examination while receiving advice from the advisor. The advisor may also be referred to as an instructor, supporter, or assistant.

The ultrasonic diagnostic device 13 will now be described in detail below. A probe (more accurately, probe head) 16 is held by the examiner. The probe 16 is a portable wave transmitting and receiving device. A wave transmitting and receiving surface of the probe 16 is applied to a surface of the subject 202, and in this state, the probe transmits and receives ultrasonic waves.

The probe 16 has a transducer array composed of a plurality of transducers arranged in one dimension. The transducer array forms an ultrasonic beam, and the ultrasonic beam is electronically scanned repeatedly. In this manner, a beam scanning surface is repeatedly formed in the subject 202.

A transmitting and receiving unit 17 is a circuit that provides the probe 16 with a plurality of transmission signals in parallel and processes a plurality of received signals that are output in parallel from the probe 16. The transmitting and receiving unit 17 outputs beam data. A plurality of pieces of beam data arranged in the electronic scanning direction form received frame data. An image forming unit 18 forms an ultrasonic image based on the received frame data. The ultrasonic image is a B-mode tomographic image, for example. Other types of ultrasonic images may be formed.

A calculation control unit 20 is composed of a processor (for example, a CPU) that executes a program. The calculation control unit 20 has a display processing unit 26. The display processing unit 26 forms an image to be displayed on a display device 24. The image includes a tomographic image in the form of moving image, a character string indicating the content of advice, an advisor image, and the like, as described in detail below in the embodiment.

The calculation control unit 20 is connected to a control panel 30 and a communication unit 22. In the examination room 10, a camera 15 is provided for capturing an image of the subject to obtain a subject image. A plurality of cameras may be provided. In the examination room 10, the camera 15 is placed at a position and orientation in which an image of a probe contact site can be captured. An imaging signal output from the camera 15 is transmitted to the calculation control unit 20.

The communication unit 22 is connected to a communication line 200. The communication line 200 is a wired or wireless line. The communication line 200 may be composed of a dedicated line, and the dedicated line may be a network.

In the embodiment, ultrasonic image data, subject image data, and other necessary data are transferred from the ultrasonic diagnostic device 13 to the remote device 14. The data to be transferred may include information about the subject, information indicating diagnostic conditions, and the like. The data to be transferred may also include response character string data described below. The control panel 30 has, for example, a trackball, switches, buttons, and a keyboard. The display device 24 is composed of an LCD, an organic EL display device, or the like. The camera 15 is a color camera for capturing a moving image.

The remote device 14 has a calculation control unit 34. The calculation control unit 34 is composed of a processor (for example, a CPU) that executes a program. The calculation control unit 34 is connected to a communication unit 32, a camera 36, a microphone 40, an inputting device 41, a display device 42, a communication unit 44, and the like.

The remote device 14 is a tablet terminal as described above. It may be composed of a notebook PC, desktop PC, or the like. The remote device 14 has a touch panel screen, and the touch panel screen constitutes the input device 41 and the display device 42.

The camera 36 and the microphone 40 are incorporated in a housing of the remote device 14. The camera 36 captures an image of the advisor. An advisor image is thus obtained. The camera 36 is again a color camera for capturing a moving image. The camera 36 transmits advisor image data to the communication unit 22 via the calculation control unit 34 and the communication unit 32. The microphone 40 converts the voice of the advisor; that is, advice, into an audio signal.

The calculation control unit 34 has a display processing unit 43, conversion unit 45, and the like. The display processing section 43 forms an image to be displayed on the display device 42. The image includes an ultrasonic image, an examiner image, a response character string, and the like. The conversion unit 45 generates an advice character string based on the audio signal. The advice character string is generated in the form of text data. The content of the advice may be expressed as a code. The entire or a part of the conversion unit 45 may be provided in the ultrasonic diagnostic device 13 or in other devices.

Specifically, the conversion unit 45 is composed of a recognition unit 46 and a character string generation unit 48. The recognition unit 46 performs speech recognition. The recognition unit 46 may be composed of a machine learning-based estimation device. The character string generation unit 48 expresses the recognized content as a text.

The communication unit 32 is connected to the communication line 200. As described below, the remote device 14 transmits text data indicating the advice character string, advisor image data, operation support image data, and the like to the ultrasonic diagnostic device 13. Specifically, the data are transmitted and received between the communication unit 22 and the communication unit 32.

The communication unit 44 is connected to a network 52. The network 52 is connected to other medical devices 54 and 56. The other medical devices 54 and 56 include, for example, a CT machine, an MRI machine, an endoscope, an image server, and the like. The display device 42 of the remote device 14 may display images obtained from the other medical devices.

Figure 2:
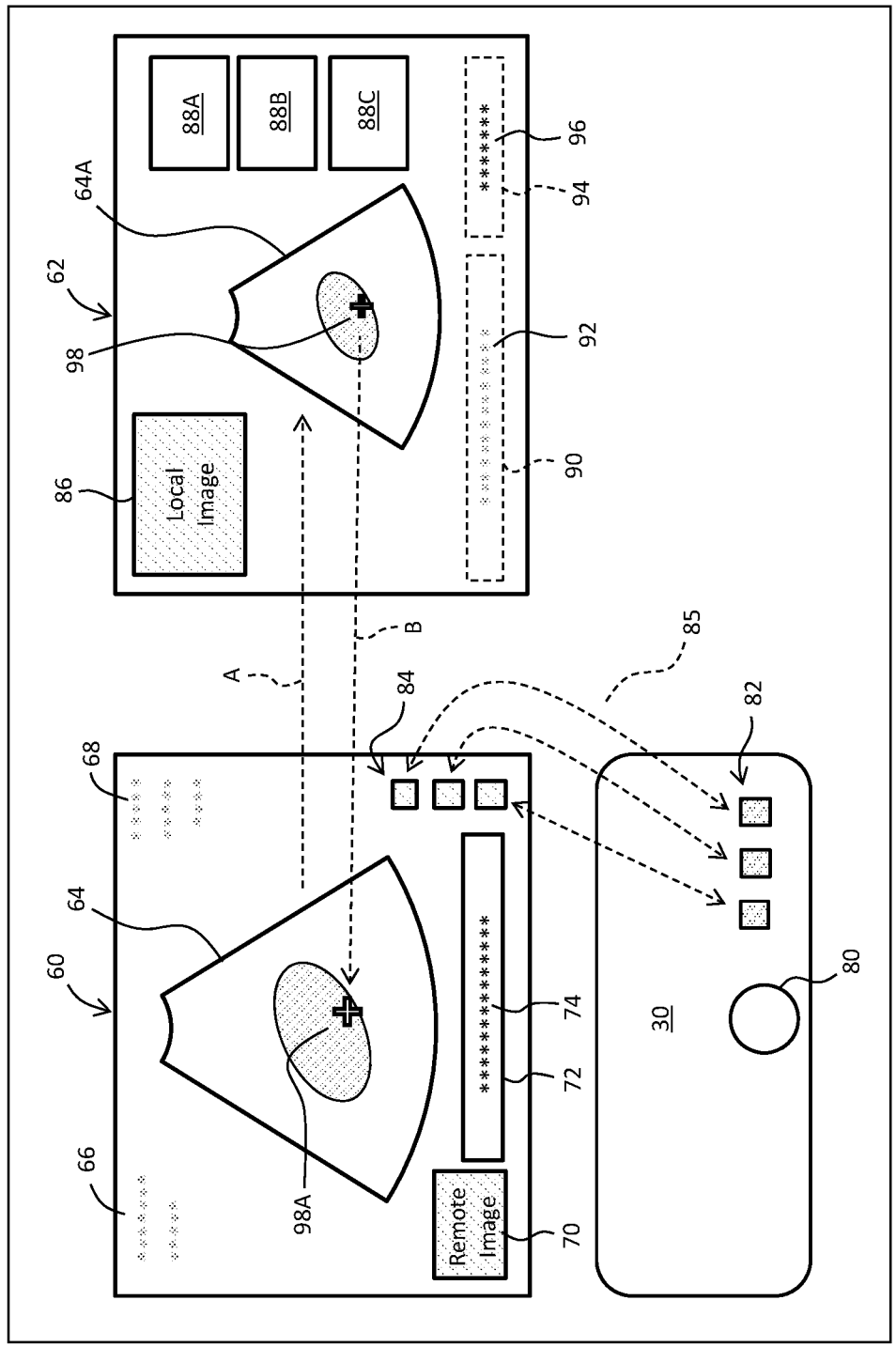
FIG. 2 is a diagram showing a first display example.

FIG. 2 shows a first display example. An image 60 is an image displayed on the display device of the ultrasonic diagnostic device. An image 62 is an image displayed on the display device of the remote device. The image 60 includes a tomographic image 64 as an ultrasonic image. As a position and posture of the probe change, the content of the tomographic image 64 changes.

The image 60 also includes an advisor image 70 as a remote image and a character string display field 72. The examiner can recognize, for example, an attitude and expression of the advisor through observation of the advisor image 70. In some cases, the advisor instructs how to operate the probe through gestures. The content of advice in the form of an advice character string 74 is displayed in the character string display field 72. The character string display field 72 is located below the tomographic image 64. The character string display field 72 is sized such that, for example, text up to 100 characters can be displayed within three lines or fewer. Display control for individual character strings will be described below. In the image 60, for example, subject information 66 and diagnostic conditions 68 are also displayed.

The control panel 30 includes a trackball 80 and a switch array 82. The trackball 80 is a pointing device. The switch array 82 is composed of a plurality of physical switches to which functions are assigned. In the embodiment, those switches are used to select fixed responses. More specifically, three switches are respectively assigned with three fixed responses in advance, and when the examiner selects a certain fixed response according to necessity, text data indicating that response is transferred from the ultrasonic diagnostic device to the remote device.

The image 60 includes a virtual button array 84 composed of a plurality of virtual buttons. The plurality of virtual buttons correspond to the plurality of switches described above (see reference numeral 85). Any one of the virtual buttons can be selected by moving a cursor by means of the trackball 80. In this manner, like in the above case, a certain fixed response can be transmitted to the remote device side.

The image 62 includes a tomographic image 64A. The tomographic image 64A is the same image as the tomographic image 64 displayed on the ultrasonic diagnostic device (see reference character A). In the illustrated configuration example, the image 62 also includes a subject image 86 as a local image. Images 88A, 88B, and 88C obtained in other medical devices may also be displayed in the image 62.

A monitoring field 90 is provided at the bottom of the image 62. In the monitoring field 90, an advice character string 92 is displayed. By checking it, the advisor can confirm that an audio signal has been converted correctly. A character string display field 94 is also provided at the bottom of the image 62. The character string display field 94 is an area for displaying a response character string. When the examiner selects a certain fixed response, a response character string corresponding to it is displayed in the character string display field 94. Displaying the advice character string and the response character string enables bi-directional, smooth communication.

When the advisor specifies the coordinates on the tomographic image 64A in the image 62 by using a pointing device or finger touch, a marker 98 is displayed there. Data of the coordinates are transferred from the remote device to the ultrasonic diagnostic device (see reference character B). A marker 98A is then displayed on the tomographic image 64. The position at which the marker 98A is displayed on the tomographic image 64 is the same as the position at which the marker 98 is displayed on the tomographic image 64A.

The advisor can use the above function to instruct the examiner about a certain site. The advisor can thus clearly communicate, for example, location of abnormality. Subject information, diagnostic conditions, and the like may also be displayed in the image 62.

Figure 3:
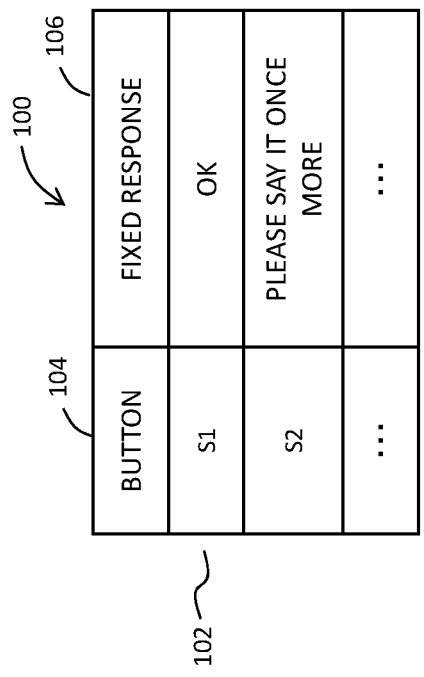
FIG. 3 is a diagram showing a list of fixed responses.

FIG. 3 shows a fixed response table 100 that is controlled by the ultrasonic diagnostic device. The fixed response table 100 includes a plurality of records 102. Each record 102 includes a button identifier 104 and a fixed response sentence 106. The content of the table 100 may be customized by the examiner, for example.

Figure 4:
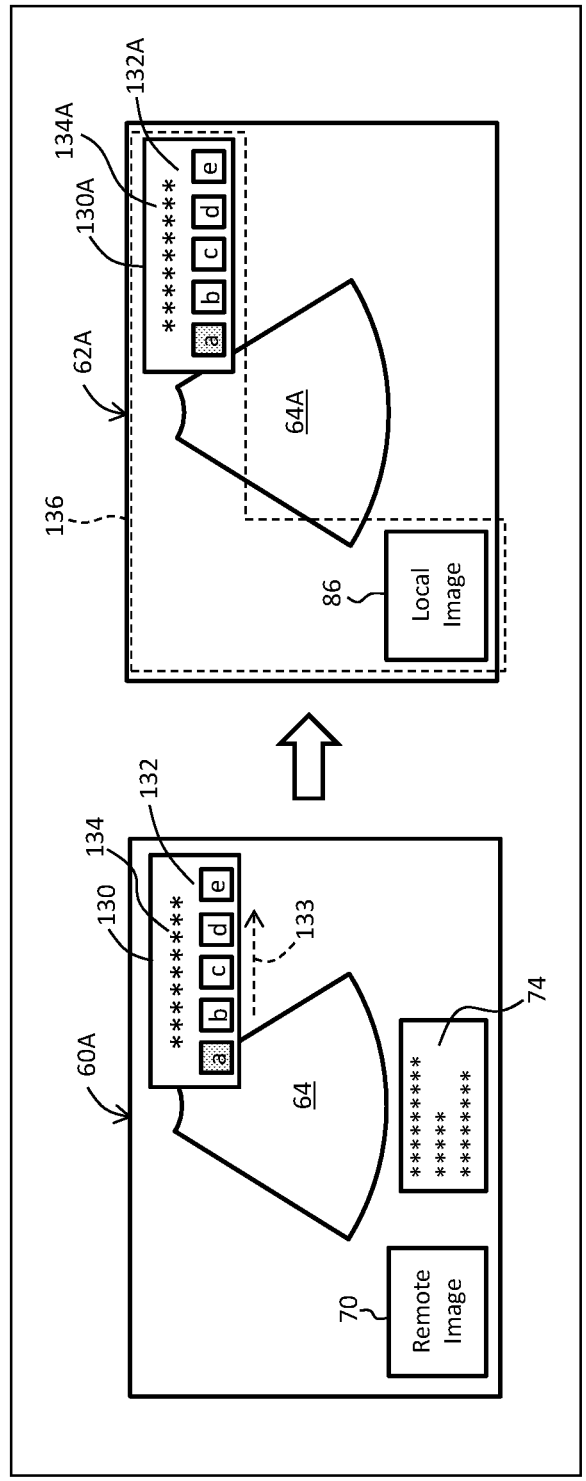
FIG. 4 is a diagram showing a second display example.

FIG. 4 shows a second display example. An image 60A is an image displayed on the ultrasonic diagnostic device, and an image 62A is an image displayed on the remote device. The image 60A includes the tomographic image 64, the advisor image 70, and the advice character string 74. The image 60A also includes a window 130 displayed in a pop-up manner through a predetermined operation. The window 130 includes an icon array 132. The array is composed of a plurality of icons, and any one of the icons can be selected by operating a trackball, for example (see reference numeral 133). A fixed response sentence 134 corresponding to the selected icon is displayed in the window 130 in the form of character string. It is also possible to select a fixed response sentence through manipulation of a pulldown menu.

Meanwhile, the image 62A includes the tomographic image 64A and the subject image 86. The image 62A also includes a window 130A. In the illustrated display example, the window 130A has the same content as the window 130. That is, the window 130A includes an icon array 132A and a fixed response sentence 134A. In this manner, the content of a response from the examiner is communicated to the advisor. As a matter of course, the two windows 130 and 130A may have different configurations.

In the illustrated configuration example, the ultrasonic diagnostic device synthesizes the window 130 and the examiner image and transfers the resulting synthesized data to the remote device. Reference numeral 136 indicates a portion corresponding to the synthesized data. In transferring data from the remote device to the ultrasonic diagnostic device, synthesized data may be transferred, instead of transferring a plurality of data pieces.

Figure 5:
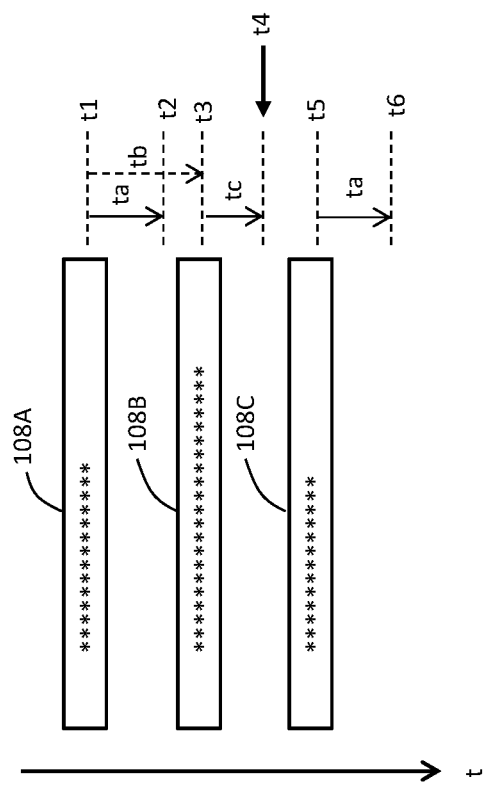
FIG. 5 is a diagram for explaining switching of display of advice character strings.

FIG. 5 shows an example of display control of advice character strings. At a timing t1, display of a first advice character string 108A is started. The display of the first advice character string 108A continues for a predetermined period ta and then automatically ends at a timing t2. At a timing t3, display of a second advice character string 108B is started. At the timing t3, the display of the first advice character string 108A may end. In this case, a period during which the first advice character string 108A is displayed is tb.

A timing t4 is a timing when a predetermined event occurs. For example, the timing 4 is a timing when the wave transmitting and receiving surface of the probe is moved away from the body surface and then left in the air. If the predetermined event occurs, an advice character string that has been displayed until then is deleted. In the illustrated example, the second advice character string 108B disappears at the timing t4. At a timing t5, display of a third advice character string is started. At a timing t6, the display of the third advice character string ends. In this case, the display period is ta. The duration of the display period ta is set in advance by the user or automatically.

Figure 6:
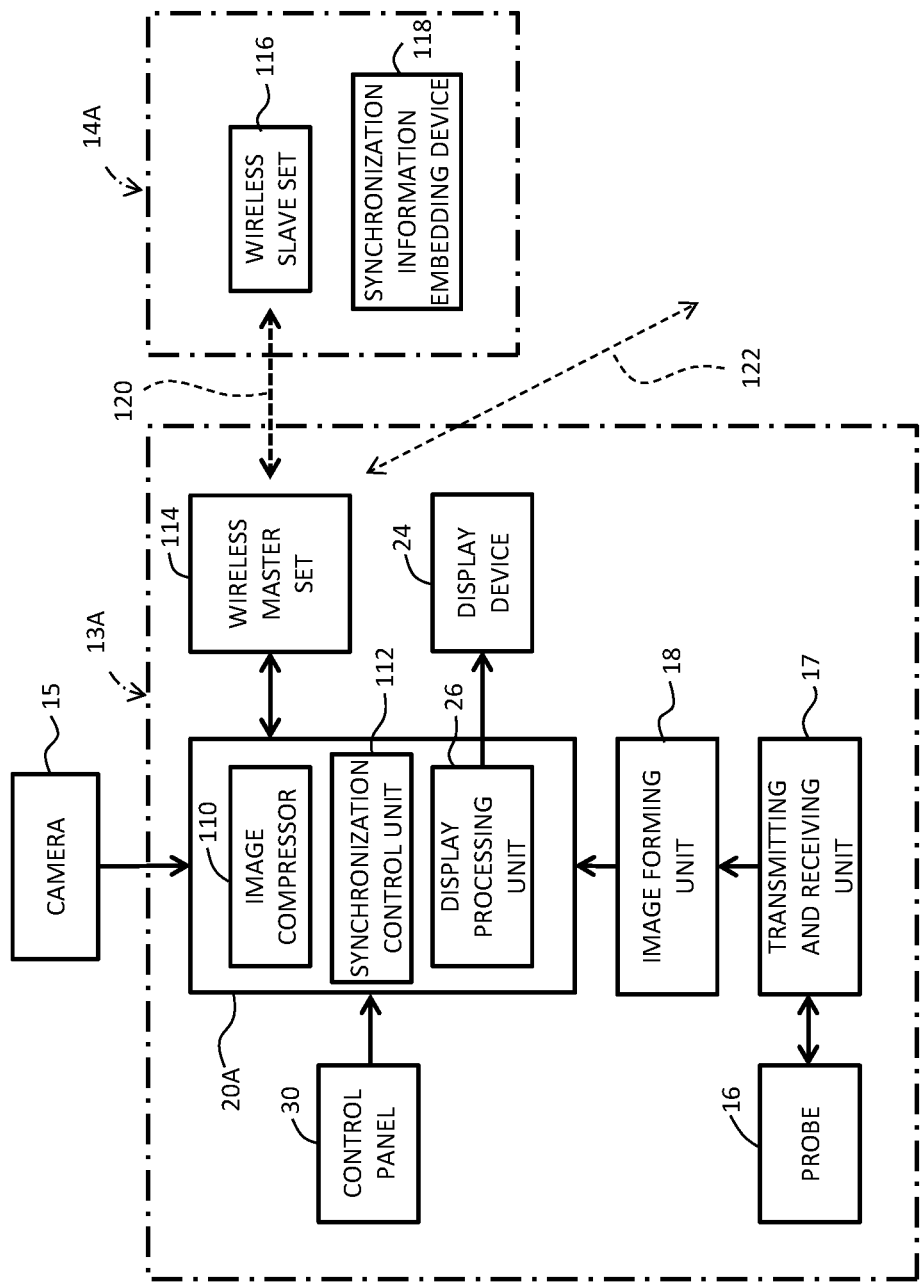
FIG. 6 is a block diagram showing a configuration of an ultrasonic diagnostic system according to a second embodiment.

FIG. 6 shows an ultrasonic diagnostic system according to a second embodiment. In FIG. 6, the elements that are illustrated in FIG. 1 are assigned the same reference numerals as in FIG. 1, and their description will be omitted.

In the second embodiment, an ultrasonic diagnostic device 13A has a wireless master set 114 that functions as a first communication unit. The wireless master set 114 is a wireless router and constitutes an access point. A remote device 14A has a wireless slave set 116 that functions as a second communication unit. The wireless slave set 116 is wirelessly connected to the wireless master set 114 (see reference numeral 120). Wireless slave sets in other devices may be connected to the wireless master set 114 (see numeral reference numeral 122).

A calculation control unit 20A of the ultrasonic diagnostic device 13A has an image compressor 110. The image compressor 110 compresses an image, such as a tomographic image, prior to transferring of the image, in order to reduce its data volume. Although the remote device 14A is provided with an image decompressor corresponding to the image compressor 110, its illustration is omitted.

The remote device 14A has a synchronization information embedding device 118. As described below, when an operation support image is transmitted together with an advice character string, a timestamp is embedded in them as synchronization information, in order to synchronize their display. In the ultrasonic diagnostic device 13A, a synchronization control unit 112 refers to the timestamp embedded in each piece of the transmitted information and performs display control such that the advice character string and the operation support image are displayed at the same time. The synchronization information may be embedded in other types of information (for example, an advisor image).

FIG. 7 shows a display example according to the second embodiment. Reference numeral 62B shows an image displayed on the display device of the remote device, and reference numeral 60B shows an image displayed on the display device of the ultrasonic diagnostic device. The image 62B includes a probe simulation image array 140. The probe simulation image array 140 is composed of a plurality of probe simulation images 142 corresponding to a plurality of types of probe operations. Each probe simulation image 142 includes a display element indicating an operation direction (arrow symbol). Each probe simulation image 142 functions as a probe operation support image.

On the touch panel screen, a certain probe simulation image is selected (see reference numeral 144) by the advisor by using finger touch of the advisor or a pointing device 146, such as a joystick. By doing so, data or a code indicating the selected probe simulation image is transmitted from the remote device to the ultrasonic diagnostic device.

The image 60B includes the advisor image 70 and the advice character string 74. It further includes a probe simulation image 142a selected by the advisor. By displaying the probe simulation image 142a in addition to the advice character string 74, it is possible to convey the content of advice to the examiner more accurately. To synchronize display of the advice character string 74 and the probe simulation image 142a, synchronization control described above is performed.

According to each of the above embodiments, because advice from the advisor is displayed on the device as a character string during ultrasonic examination, the content of advice is not easily conveyed to the subject, and the possibility that the subject feels anxious can be reduced. In addition, compared to the case where advice is given orally, the examiner feels less stress. By additionally providing an advisor image to the examiner, information in addition to just the advice character string can be provided to the examiner. Similarly, by providing a subject image to the advisor, the advisor can understand an actual situation of probe operation. Further, by displaying an operation support image together with the advice character string, the examiner can easily understand the content of the advice (in particular, direction indication).

The invention claimed is:

1. An ultrasonic diagnostic system comprising:
   an ultrasonic diagnostic device operated by an examiner, the ultrasonic diagnostic device comprising
      a probe that transmits and receives ultrasonic waves,
      a first display device that displays an ultrasonic image based on the ultrasonic waves that are received via the probe, and
      a first communication unit that transmits image data for the ultrasonic image; and
   a remote device that is at a remote site and is connected to the ultrasonic diagnostic device via a communication line and operated by an advisor who gives advice to the examiner, the remote device at the remote site comprising
      a second communication unit that receives the image data transmitted from the first communication unit of the ultrasonic diagnostic device,
      a second display device that displays the ultrasonic image based on the received image data,
      a remote camera that is at the remote site and obtains advisor image data corresponding to an advisor image of the advisor, the advisor image data from the remote camera being transmitted from the second communication unit of the remote device to the first communication unit of the ultrasonic diagnostic device,
      a microphone that converts a voice of the advisor to an audio signal, and
      a conversion unit that is provided in the remote device and that converts the audio signal to an advice character string, the advice character string being text data converted from the audio signal representing the voice of the advisor,
   wherein data indicating the advice character string is transmitted from the second communication unit of the remote device to the first communication unit of the ultrasonic diagnostic device,
   wherein the advice character string corresponding to advice from the advisor is displayed along with the advisor image of the advisor on the first display device of the ultrasonic diagnostic device while ultrasonic examination is being performed by the examiner,
   wherein the ultrasonic diagnostic device further includes
      a plurality of response elements to be selected by the examiner, the plurality of response elements being physical buttons or virtual buttons displayed on the first display device, and
      a response table including a plurality of pieces of response information corresponding to the plurality of response elements,
   wherein response information selected from the plurality of pieces of response information according to a response element selected from the plurality of response elements is transmitted from the first communication unit to the second communication unit, and
   wherein a response character string corresponding to a response from the examiner is displayed on the second display device based on the response information.

2. The ultrasonic diagnostic system according to claim 1, further comprising a local camera that captures an image of a subject to which the probe is applied and obtains a subject image, wherein subject image data output from the local camera are transmitted from the first communication unit to the second communication unit, and the subject image is displayed on the second display device together with the ultrasonic image.

3. The ultrasonic diagnostic system according to claim 1, wherein an operation support image selected by the advisor is displayed on the first display device together with the advice character string.

4. An ultrasonic diagnostic device operated by an examiner, the ultrasonic diagnostic device being connected, via a communication line, to a remote device operated by an advisor who gives advice to the examiner, the ultrasonic diagnostic device comprising:
   a probe that transmits and receives ultrasonic waves;
   a display device that displays an ultrasonic image generated by transmitting and receiving the ultrasonic waves;
   a communication unit that transmits image data for displaying the ultrasonic image to the remote device and receives character string data representing a voice of the advisor from the remote device;
   a plurality of response elements to be selected by the examiner, the plurality of response elements being physical buttons or virtual buttons displayed on the display device; and
   a response table including a plurality of pieces of response information corresponding to the plurality of response elements,
   wherein data which represents an advice character string corresponding to the character string data representing the voice of the advisor is received by the communication unit from the remote device,
   wherein the advice character string corresponding to advice from the advisor is displayed along with an advisor image of the advisor on the display device of the ultrasonic diagnostic device while ultrasonic examination is being performed by the examiner,
   wherein response information selected from the plurality of pieces of response information according to a response element selected from the plurality of response elements is transmitted from the communication unit to the remote device, and
   wherein a response character string corresponding to a response from the examiner is displayed on the remote device based on the response information.

5. A remote device operated by an advisor who gives advice to an examiner, the remote device being connected, via a communication line, to an ultrasonic diagnostic device operated by the examiner, the remote device comprising:
   a microphone that converts a voice of the advisor to an audio signal;
   a conversion unit that converts the audio signal to character string data;

a communication unit that receives image data from the ultrasonic diagnostic device and transmits the character string data to the ultrasonic diagnostic device;

a display device that displays the ultrasonic image based on the image data; and a camera that obtains an advisor image of the advisor, advisor image data corresponding to the advisor image from the camera being transmitted from the communication unit of the remote device to the ultrasonic diagnostic device, wherein data which represents an advice character string corresponding to the character string data converted from the audio signal representing the voice of the advisor is transmitted from the communication unit to the ultrasonic diagnostic device, wherein the advice character string corresponding to advice from the advisor is displayed along with an advisor image of the advisor on a display device of the ultrasonic diagnostic device while ultrasonic examination is being performed by the examiner, wherein response information, selected from a plurality of pieces of response information according to a response element selected from a plurality of response elements displayed on the ultrasonic diagnostic device, is received by the communication unit from the ultrasonic diagnostic device, and wherein a response character string corresponding to a response from the examiner is displayed on the display device based on the response information.

* * * * *